United States Patent
Gross

[11] Patent Number: 5,397,313
[45] Date of Patent: Mar. 14, 1995

[54] LOW FRICTION SYRINGE

[75] Inventor: James R. Gross, Wareham, Mass.

[73] Assignee: The Kendall Company, Mansfield, Mass.

[21] Appl. No.: 187,034

[22] Filed: Jan. 27, 1994

[51] Int. Cl.⁶ ........................................... A61M 5/315
[52] U.S. Cl. ...................................... 604/218; 604/230
[58] Field of Search ............... 604/187, 218, 219, 222, 604/230

[56] References Cited

U.S. PATENT DOCUMENTS

| | | | |
|---|---|---|---|
| 2,886,034 | 5/1959 | Robinson et al. | 604/222 |
| 3,135,260 | 6/1964 | Hamilton | 604/222 |
| 3,176,595 | 4/1965 | Schwartz | 604/222 |
| 4,212,309 | 7/1980 | Moorehead | 604/222 |
| 4,266,557 | 5/1981 | Merry | 604/222 |
| 4,405,249 | 9/1983 | Scales | 604/222 |
| 4,986,820 | 1/1991 | Fischer | 604/218 |

FOREIGN PATENT DOCUMENTS 0870669  6/1961  United Kingdom ................ 604/218

*Primary Examiner*—John D. Yasko
*Attorney, Agent, or Firm*—Alvin Isaacs

[57] ABSTRACT

The invention features a low friction syringe which includes a plastic barrel having a circumferential inner surface defining a chamber, a plastic plunger having a distal end received in the barrel chamber, and an elastomeric gasket positioned at the distal end of the plunger and received in the barrel chamber. The gasket comprises a body with forward and rearward ends and first and second annular flanges positioned circumferentially at the forward and rearward ends of the body. The forward flange permits injection to occur. The rearward flange permits aspiration to occur. The flanges are separated by an annular space intermediate the body portion and the barrel inner surface. The gasket also includes an annular projection extending from each flange. Each projection is of reduced thickness relative to the thickness of each flange itself and provides a contact point with the barrel inner surface when the plunger distal end is received in the barrel chamber, thereby enabling reduced frictional contact with the barrel inner surface during forward and rearward movement of the gasket.

6 Claims, 4 Drawing Sheets

LOW FRICTION SYRINGE

FIELD OF THE INVENTION

The invention relates to syringes in general and in particular to syringes useful in certain sensitive medical procedures.

BACKGROUND OF THE INVENTION

During medical procedures such as administration of an epidural anesthetic, it is necessary to position the tip of a needle at a relatively precise position inside the patient's body. During procedures involving epidural anesthesia, the needle tip is located in the potential epidural space. If the needle tip has been advanced too far into the body, it projects through the dura mater into the subarachnoid space, creating an opening out of which cerebral spinal fluid may leak, the leakage being associated with post-dural puncture headache. A ground glass syringe is often utilized in this procedure to determine the location of the needle tip through the use of pressure variations within various body spaces. Because a syringe is normally considered a disposable item, it is desirable to reduce its cost to the hospital and patient below that of the relatively expensive ground glass syringes. Glass syringes have a propensity to break if dropped, and have been know to freeze in position in the barrel, necessitating immediate replacement with a new syringe before continuation of the procedure.

A need exists for a syringe which will ease the demands placed on the anesthesiologist's dexterity in performing administration of an epidural anesthetic without resort to unfamiliar devices which require special handling or are difficult to use, and while providing the sensitivity of feel that glass syringes are known for. The precision fit between a glass plunger and a glass barrel confers a sensitive feel to the user when air or liquid flows into or exits the syringe. The frictional resistance between the glass plunger and glass barrel is very low and thus a change in pressure inside the syringe barrel is communicated to the user by a corresponding movement of the plunger. Conversely, the frictional resistance between an elastomeric plunger tip and a plastic syringe barrel is very high due to drag created by rubbing of the outer diameter of the plunger tip against the inner diameter of the plastic barrel during movement.

There is a need in the art for, and thus it is one object of the invention to provide, a plastic syringe which has the sensitive feel and low resistance of a glass syringe.

It is also an object of the invention to provide a simple, reliable, inexpensive modification of a conventional syringe, in particular for use with syringes of the so-called "loss of resistance" type which are specifically designed for low barrel friction to facilitate kinesthetic sensing of changes in plunger resistance to injection as the needle passes through various anatomical structures.

U.S. Pat. No. 4,266,557, to Merry, describes a low friction syringe in which the forward and rearward ends of the gasket portion of the plunger includes first and second annular flanges, respectively. Each flange narrows into a hinge region and then widens into an enlarged lip. The enlarged lip flexes at the hinge region and relative to the remainder of the flange. The low resistance syringe of the invention is an improvement over the low resistance syringe described in U.S. Pat. No. 4,266,557 in that the syringe of the invention contains an annular projection extending from each flange and of reduced thickness relative to the thickness of the flange, instead of the narrow hinge region and wider enlarged outer lip of the '557 patent. The resultant reduced drag of the annular projections on the inner surface of the barrel in the syringe of the invention is an improvement with respect to sensitivity and feel, and thus also with respect to detecting loss of resistance in delicate procedures such as location of the epidural space.

SUMMARY OF THE INVENTION

The invention features a low friction syringe, including a plastic barrel having a circumferential inner surface defining a chamber; a plastic plunger having a distal end received in the barrel chamber; and an elastomeric gasket positioned at the distal end of the plunger and received in the barrel chamber, the gasket comprising a body with forward and rearward ends and first and second annular flanges positioned circumferentially at the forward and rearward ends of the body, the flanges being separated by an annular space intermediate the body portion and the barrel inner surface, wherein the gasket further comprises an annular projection extending from each flange, each projection being of reduced thickness relative to the thickness of each flange and providing a contact point with the barrel inner surface when said plunger distal end is received in said barrel chamber, thereby enabling reduced frictional contact with said barrel inner surface during forward and rearward movement of said gasket.

As used herein, "projection" refers to an extension, and "of reduced thickness" refers to any thickness less than the thickness of the flange when the flange and projection are measured either in longitudinal cross-section or in annular cross-section; preferably the projection thickness will be less than one-half, more preferably less than one-quarter, of the thickness of the flange itself. The term "projection" does not encompass a tapered portion of the flange itself. "Reduced frictional contact" refers to less friction than is produced during movement of an enlarged portion of an annular flange against the inner surface of a syringe barrel.

One advantage of the present invention is the provision of an improved syringe of simplified construction and reduced cost.

An important feature of the present invention is that the gasket flanges, by virtue of the flange projections, have minimal resistance for the syringe barrel to permit relatively free movement of the gasket and plunger as they slide through the barrel.

Yet another feature of the invention is that the annular gasket projections flex with respect to the flanges from which they project during movement of the plunger forward or rearward along the inner surface of the barrel. This flexibility provides for reduced drag and, consequently, exceedingly smooth movement of the gasket along the inner surface of the barrel. These properties translate into increased sensitivity of feel for the user of the low friction syringe.

A further feature of the invention is that syringes described herein confer high sensitivity similar to a glass syringe, while being less costly than glass. In addition, syringes of the invention provide low friction movement of the plunger with respect to the inner surface of the barrel. Because of these qualities, the present invention is intended to overcome the difficulties and disadvantages associated with the many previous attempts to facilitate administration of anesthesia. Given the potential for irreparable, catastrophic injury if the needle is mishandled, any aid which will increase the confidence of the anesthesiologist in locating the epidural space is of great value.

Therefore, the invention also features methods of detecting loss of resistance, the method comprising the steps of providing a low friction syringe, as described herein, in operative association with a needle, wherein the plunger is inserted within the barrel chamber of the syringe; inserting the needle through the patient's skin and into a body cavity, wherein a change in pressure in the syringe barrel chamber is sufficient to cause an indication of loss of resistance.

Preferably, forward or rearward movement of the syringe plunger in the barrel is effected by a change in pressure within the barrel chamber.

The invention also includes a method of locating the epidural space of a patient, the method comprising providing a low friction syringe, as described herein, in operative association with an epidural needle, wherein the plunger is inserted within the barrel chamber of the syringe and air or fluid is contained within the barrel chamber; advancing the epidural needle through the supraspinous, interspinous and ligamentum flavum tissues of the patient; and assessing for entry of the needle into the epidural space by determining loss of resistance to injection of the air or fluid. As used herein, the ability to detect "loss of resistance" refers to the kinesthetic sensing of changes in plunger resistance to injection.

A further feature of the invention is that the gasket includes both forward and rearward projections, the forward projection being involved in particular in injection, and the rearward projection being involved in particular in aspiration. The combination of forward and rearward projections permits the low friction syringe of the invention to be used in every manner and way that a glass syringe is used.

Further features will become more fully apparent in the following description of the embodiments of this invention and from the appended claims.

DETAILED DESCRIPTION OF THE INVENTION

Figure 1:
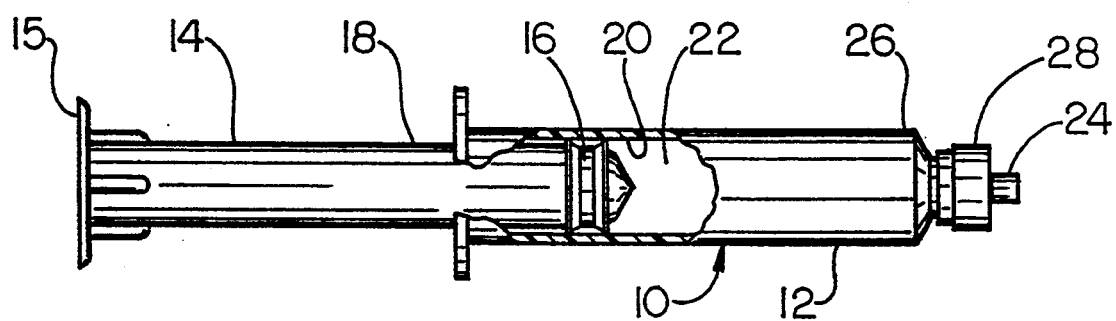
FIG. 1 is an elevational view, partly broken away, of a low friction syringe of the present invention.

Referring now to FIG. 1, there is shown a syringe generally designated 10 having a barrel 12, an elongated plunger 14, and a gasket 16 of elastic material secured to a distal end 18 of the plunger 14. Plunger 14 also has a thumb-receiving end 15 where pressure is applied to push the gasket 16 end of plunger 14 into barrel 12. The syringe barrel 12 has an inner surface 20 defining a chamber 22, a tip 24 at a proximal end 26 of the barrel, and a conventional luer slip tip or luer lock 28 for securement of the syringe barrel to a suitable instrument, such as a needle (not shown). Gasket 16 is slidably received in the barrel chamber 22. The plunger gasket forms a light seal between the plunger and the syringe barrel inner surface. The syringe is thus useful for kinesthetic sensing of change in pressure within chamber 22.

Figure 2:
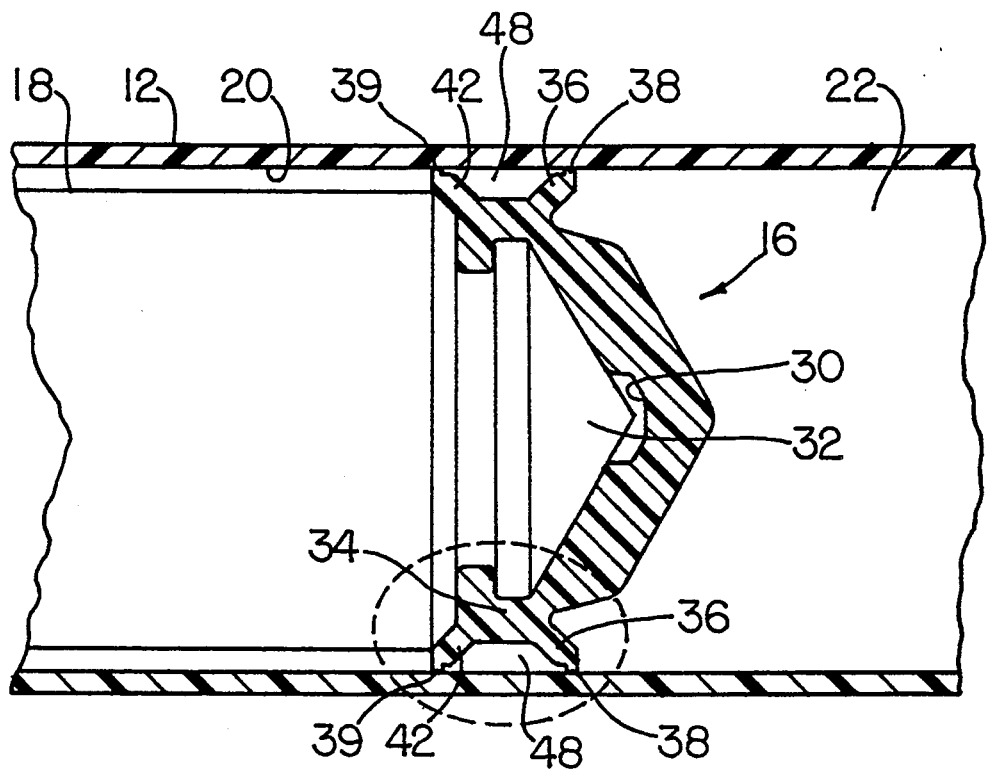
FIG. 2 is an enlarged cross-sectional view of a portion of the syringe of FIG. 1.
Figure 3:
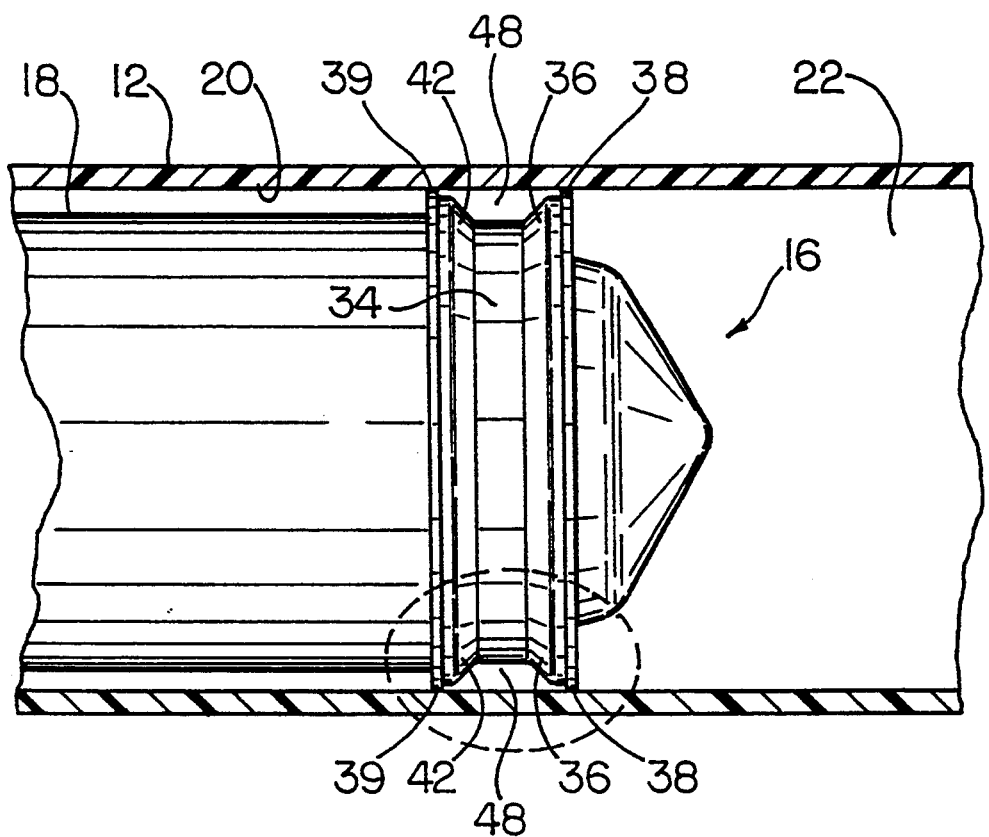
FIG. 3 is an enlarged elevational view of a portion of the syringe of FIG. 1.
Figure 4:
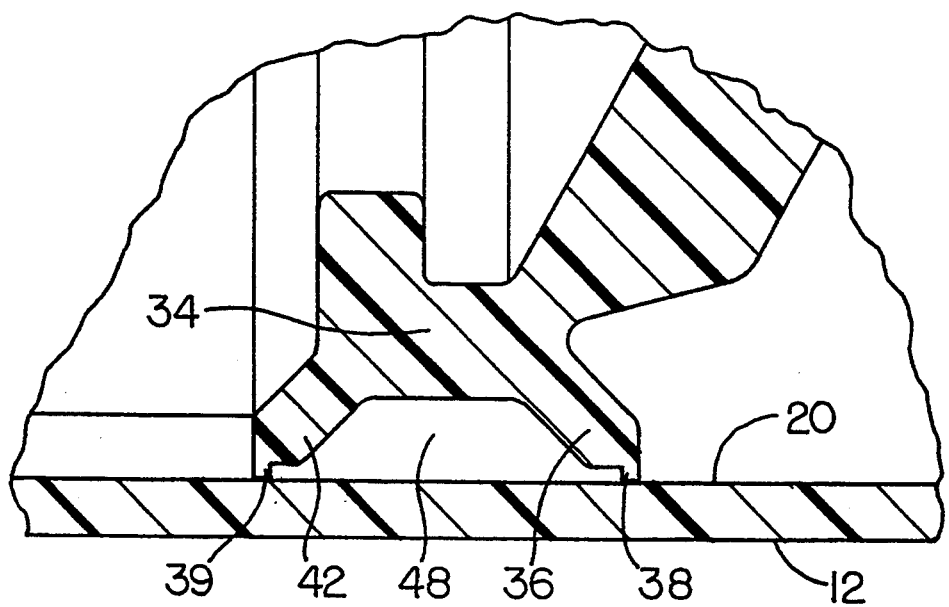
FIG. 4 is an enlarged view of a portion of the syringe of FIG. 2.
Figure 5:
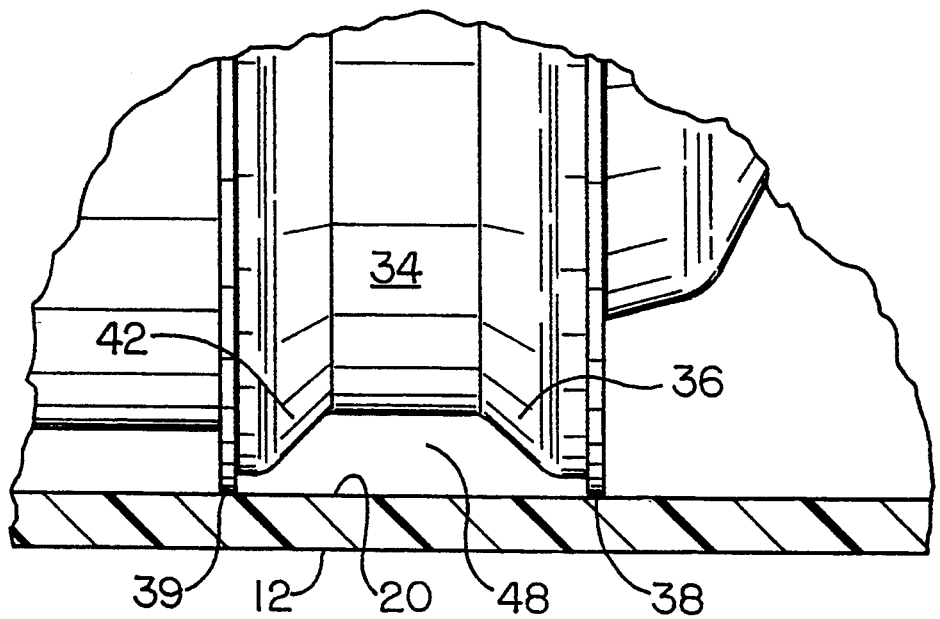
FIG. 5 is an enlarged view of a portion of the syringe of FIG. 3.
Figure 6:
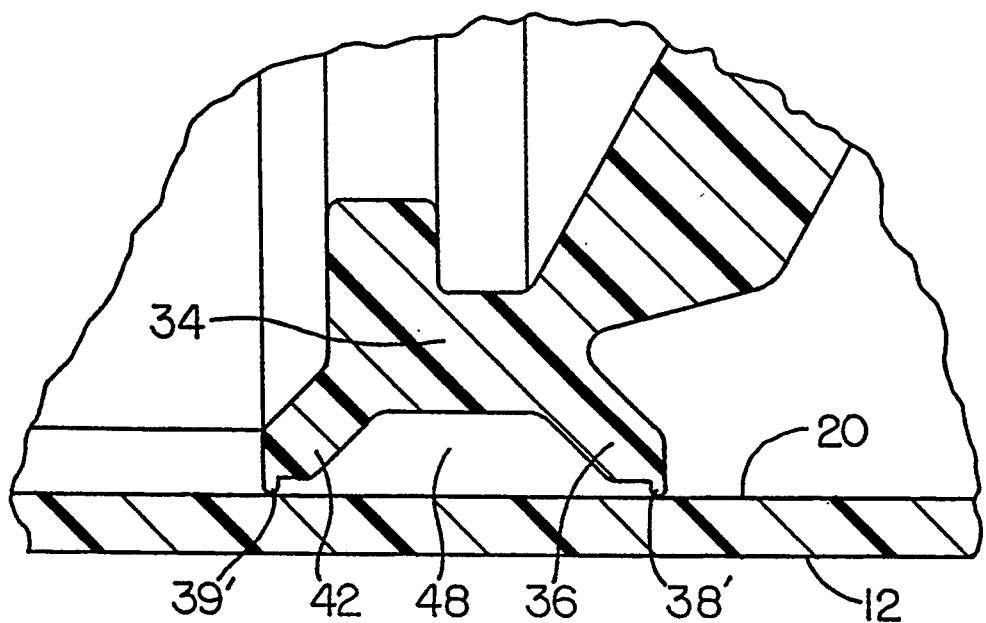
FIG. 6 is an enlarged view of a portion of the syringe of FIG. 3 showing a circular flange projection.

An enlarged view of a portion of gasket 16 slidably positioned within barrel 12 is shown in FIG. 2, with another enlargement of a portion of the FIG. 2 gasket shown in FIG. 4. An enlarged sideview of gasket 16 slidable positioned within barrel 12, with barrel 12 partly cut away, is shown in FIG. 3, with another enlargement of a portion of the FIG. 3 gasket shown in FIG. 5. Referring to FIGS. 1–5, gasket 16 has a main body portion 34 defining a recess 30 which receives a boss 32 projecting forwardly from the distal end 18 of the plunger 14 in order to secure the gasket 16 onto the distal end 18 of the plunger. The gasket 16 has a first annular flange 36 extending outwardly from body portion 34 in the syringe chamber, with the first flange 36 having a surface projection 38 which lightly contacts the inner surface 20 of the syringe barrel 12. Projection 38 has a reduced thickness relative the thickness of flange 36. Gasket 16 also has a second annular flange 42 extending outwardly from the body portion 34, with the second flange 42 also having a projection 39 which lightly contacts the inner surface 20 of the syringe barrel 12 and also has a reduced thickness relative the thickness of flange 42.

Projections 38, 39 may be of any shape suitable for creating drag with respect to the inner surface of chamber 22, e.g., in cross-section, a square, circular, etc., extension of each flange. Preferably, each projection is an integral piece with a flange. However, projections 38, 39 are not simply tapered tips of the flanges, since they flex relatively independently of the flanges, i.e., they possess a combination of flexibility and rigidity with respect to the flanges that allow the flanges to lightly contact the barrel inner surface during movement of the plunger in the barrel. At its outer edge, a projection preferably will not extend beyond the outer edge of the flange from which it extends. That is, the leading edge of projection 38, i.e., the edge that is perpendicular to the inner surface 20 of the syringe barrel 12 and thus which defines barrel chamber 22, will not extend beyond and thus will be coincident with the leading edge of flange 36. Similarly, the trailing edge of projection 39, i.e., the edge that is perpendicular to inner surface 20, will not extend beyond and thus will be coincident with the trailing edge of flange 42. Flanges 36 and 42 are identical except for their relative positions on gasket 16, i.e., they are mirror images of each other. As shown, the first and second flanges 36,42 define an annular space 48 intermediate the body portion 34 and the inner surface 20 of the barrel 12. While the boundary of flange 36 that defines space 48 is tapered up to projection 38 and 39, respectively, the point of juncture of projection 38 and flange 36 or projection 39 and flange 42 is angled rather than tapered, and preferably forms an angle on the order of 30°–90°.

The property of low resistance in syringes of the invention is obtained by virtue of the contact of projections 38, 39 with the inner surface 20 of the syringe barrel 12. The contact between projections 38, 39 and inner surface 20 confers relatively low friction upon movement of the gasket 16 in the barrel 12 and allows for continuous formation followed by breakage and re-formation of a light seal between the elastomeric gasket and the plastic barrel, permitting relatively free movement of the plunger and gasket in the syringe barrel, while maintaining enough pressure within the barrel chamber 22 to allow for detection of loss of resistance.

The advantage of the low friction syringe of the invention over other syringes known in the art is evident in the comparative force required to move the plunger within the barrel. The force required to move the plunger within the barrel for a syringe in which the plunger lacks projections 38, 39 was tested and found to be 0.2786 lbs. In contrast, consistently reduced force was required to move the plunger of the low friction syringe of the invention, i.e., containing projections 38, 39, within the barrel: 0.1361 lbs.

The projection/flange arrangement unique to the syringe gasket described herein confers additional advantageous properties to the low resistance syringes of the invention. The forward projection/flange arrangement is particularly effective for injection, and the rearward projection/flange arrangement is particularly effective in aspiration. The combination of forward and rearward projections permits a low friction syringe of the invention to be used in every manner and way that a glass syringe is used. For example, testing was performed to compare the effectiveness of aspiration of a low friction syringe of the invention and a syringe having a gasket containing a single flange. The results showed that the low friction syringe of the invention aspirated 100% of the barrel volume, whereas the single flange syringe aspirated only 50% of the syringe volume. Thus, a syringe of the invention, by virtue of the presence of both forward and rearward projection/flange combinations, is particularly useful in performing critical medical procedures involving aspiration, e.g., administration of epidural anesthesia.

Thus, the syringe of the present invention may be utilized in special medical procedures, such as an epidural anesthesia procedure, where free movement of the syringe plunger in the barrel is required, previously accomplished by precision ground glass syringes. The syringe barrel 12 and plunger 14 may be made from relatively inexpensive plastic materials, such as polycarbonate, which is transparent and provides a clear view into the syringe barrel, while the syringe gasket 16, including projections 38, 39, may be constructed from inexpensive elastomers, such as polyisoprene rubber. Gasket body 34, flanges 36, 42, and projections 38, 39 may be formed as an integral elastomeric piece, e.g., by injection or transfer molding. Thus, the syringe of the present invention may be constructed in a simplified manner from inexpensive parts, while accomplishing results of relatively expensive ground glass syringes.

Thus, in accordance with the present invention, the syringe provides relatively free movement of the plunger and gasket along the syringe barrel under conditions of relatively low friction between the gasket and barrel in order to permit use of the syringe in special medical procedures, as previously described. Further, the syringe of the invention permits easy detection of loss of resistance by virtue of the minimal contact of the gasket projections with the barrel's inner surface.

In use, e.g., in administration of epidural anesthesia, the syringe is operated as follows.

Administration of epidural anesthesia involves the location of the epidural space which surrounds the dura mater which in turn surrounds the spinal cord proper. The epidural space is between the ligamentum flavum and the dura mater, and is a layer of fatty, highly vascularized tissue separating the ligamentum flavum and the dura mater. These flexible but tough ligaments interconnect the bony vertebrae which enclose and protect the spinal cord and spinal canal. A dose of a suitable anesthetic such as lidocaine or bupivacaine, by way of example, produces a regional nerve block suitable for surgical procedures to be performed on portions of the anatomy affected by the nerve block, primarily but not limited to nerves located at the level of the spinal column at which the anesthetic is injected.

In order to appreciate the contribution being made by the present invention, it is important to understand the demands placed upon the anesthesiologist's dexterity by this procedure. In the preferred midline technique, the epidural needle passes through the supraspinous, interspinous and ligamentum flavum structures before entering the epidural space. It is of critical importance that the needle traverse the tough ligamentum flavum in a carefully measured and controlled manner. Insertion of the needle into the epidural space is complicated by the feedback as to the position of the needle tip, coupled with the imperative need to avoid puncturing the dura mater which surrounds the spinal cord, since there is potential for catastrophic trauma to the spinal cord with the epidural needle. Extreme caution must therefore be exercised in the positioning of the needle tip, which must pierce through the tough, resilient, leather-like ligamentum flavum and then stop immediately within the narrow epidural space, short of puncturing the dura mater.

The needle must be moved through the ligamentum flavum very slowly and in a carefully controlled fashion. At the same time, pressure is applied to the plunger of the attached syringe which is filled either with air or saline solution. Typically, forward movement is applied to the advancing needle with the anesthesiologists's dominant hand (the right-hand if the anesthesiologist is right-handed), while the non-dominant hand applies pressure to the plunger to test for resistance to injection. Variations of this technique may be adopted according to personal preference, for example the needle may be advanced continuously while testing for resistance, or in the alternative, the needle is advanced in very small increments, e.g. 1 millimeter, testing for resistance to injection after each advance. The object is to continuously test for loss of resistance to injection, experienced as significant movement of the plunger in response to the needle lumen entering the epidural space after clearing the ligamentum flavum. This loss of resistance is experienced by little if any resistance to injected air or fluid, and a negative aspiration test then indicates that the needle lumen is properly positioned in the epidural space.

The difficulty of correctly positioning the needle lumen in the epidural space has spurred many attempts to develop methods and devices for detecting and indicating correct needle placement. These expedients have generally exploited the low resistance to injection characteristic of the epidural space. One such technique involves placement of a drop of saline solution on the open hub of an epidural needle when the needle is inserted therein. The drop will be "sucked-in" as the needle lumen enters the epidural space. Other means used for this purpose include capillary attachments with fluid indicators developed by Odom, or inflated balloons by Macintosh, which deflate upon entering the epidural space. Such expedients are not necessary using low resistance syringes of the invention, because the contribution of the present invention is to provide for exceedingly low resistance in the syringe such that any change in pressure, or loss of resistance, is immediately apparent from the feel of the syringe to the anesthesiologist.

Thus, according to the invention, a needle is attached to the low resistance syringe of the invention, the syringe preferably containing air or fluid, with the plunger 14 positioned approximately half-way into the barrel 12, the needle is slowly advanced through the body tissues. The air or fluid will remain in the syringe during advancement of the needle through the tissues. However, upon advancement of the needle through the ligamentum flavum, and as the needle tip reaches the epidural space, a change in pressure will occur in the syringe and lumen of the needle. The change in pressure causes the air or fluid to be injected into the epidural space. This plunger movement indicates loss of resistance. Thus, the change in differential pressure within the syringe itself and between the inner chamber of the syringe and the patient's epidural space are easily detected using the exceedingly low resistance syringe described herein.

OTHER EMBODIMENTS

Other embodiments will be evident to those of skill in the art. It should be understood that the foregoing detailed description is provided for clarity only and is merely exemplary. The spirit and scope of the present invention are not limited thereto, being defined by the claims set forth below.

I claim:

1. A low friction syringe, comprising:
    a plastic barrel having a circumferential inner surface defining a chamber;
    a plastic plunger having a distal end received in the barrel chamber; and
    an elastomeric gasket positioned at the distal end of the plunger and receivable in the barrel chamber, the gasket comprising a body with forward and rearward ends and first and second annular flanges positioned circumferentially at the forward and rearward ends of the body, respectively, the flanges being separated by an annular space intermediate the body and the barrel inner surface, wherein the gasket further comprises an annular projection extending from each flange, each projection being of reduced thickness relative to the thickness of each flange and providing a contact point with the barrel inner surface when said plunger distal end is positioned in said barrel chamber, thereby enabling reduced frictional contact with said barrel inner surface during forward and rearward movement of said gasket.

2. The low friction syringe of claim 1 wherein each said projection is sufficiently flexible relative to the flanges to permit the flanges to contact the inner surface of the barrel during movement of the gasket forward or rearward in the barrel.

3. The low friction syringe of claim 2 wherein said projections are sufficiently rigid to prevent the flanges from contacting the inner surface of the barrel while the plunger is at rest.

4. The low friction syringe of claim 1, each said projection being substantially circular in cross-section.

5. The low friction syringe of claim 1, each said projection being substantially square in cross-section.

6. The low friction syringe of claim 2, said barrel chamber having a capacity for a given volume or air or liquid, wherein said forward and rearward annular projections are sufficiently flexible to permit injection or aspiration of said volume of air or liquid.

* * * * *